(12) United States Patent
Halid

(10) Patent No.: US 6,848,121 B1
(45) Date of Patent: Feb. 1, 2005

(54) PROTECTIVE UNDERPANTS AND METHOD FOR PRODUCING THE SAME

(75) Inventor: Michael P. Halid, St. Gallen (CH)

(73) Assignee: I.M.E.C. medizinische Textilien GmbH, Gallen (CH)

( * ) Notice: Subject to any disclaimer, the term of this patent is extended or adjusted under 35 U.S.C. 154(b) by 0 days.

(21) Appl. No.: 09/786,131
(22) PCT Filed: Jun. 30, 2000
(86) PCT No.: PCT/CH00/00354
   § 371 (c)(1),
   (2), (4) Date: Jun. 17, 2003
(87) PCT Pub. No.: WO01/01911
   PCT Pub. Date: Jan. 11, 2001

(30) Foreign Application Priority Data

Jul. 1, 1999 (CH) .............................. 1216/99

(51) Int. Cl.$^7$ ................................. A41B 9/00
(52) U.S. Cl. ............................. 2/400; 2/403
(58) Field of Search ............... 2/400–408, 67, 2/69, 228, 227, 238, 78.1–78.4; 604/385.25, 385.29, 385.3, 392, 394, 396

(56) References Cited

U.S. PATENT DOCUMENTS

| 1,314,799 | A | * | 9/1919 | Guinzburg ..................... 2/400 |
| 1,937,899 | A | * | 12/1933 | Le Coney ....................... 2/406 |
| 2,977,957 | A | | 4/1961 | Clyne |
| 3,237,625 | A | * | 3/1966 | Johnson ....................... 604/396 |
| 3,613,687 | A | * | 10/1971 | Kennedy ..................... 604/396 |
| 3,852,828 | A | * | 12/1974 | Silverstein ..................... 2/401 |
| 4,351,340 | A | * | 9/1982 | McLeod ..................... 604/387 |
| 4,573,987 | A | * | 3/1986 | Lamb, Jr. ..................... 604/378 |
| 4,690,681 | A | | 9/1987 | Haunschild et al. |
| 4,695,279 | A | | 9/1987 | Steer |
| 5,546,607 | A | * | 8/1996 | Roberts ......................... 2/406 |
| 5,669,902 | A | | 9/1997 | Sivilich |
| 5,745,922 | A | | 5/1998 | Rajala et al. |
| 6,487,727 | B1 | * | 12/2002 | Harsant ......................... 2/400 |

FOREIGN PATENT DOCUMENTS

| WO | WO 96/36248 A1 | 11/1996 |
| WO | WO 98/43503 A1 | 10/1998 |

* cited by examiner

Primary Examiner—Gloria M. Hale
(74) Attorney, Agent, or Firm—Browdy and Neimark, P.L.L.C.

(57) ABSTRACT

Protective pants having an outer part and an inner part each of which include two mutually opposite side parts engaged to a central part, wherein the central part is made with a first and a second elongated section, the first elongated section being longer than the second elongated section and joined to the second elongated section on the front side of the protective pants.

7 Claims, 6 Drawing Sheets

180
PROTECTIVE UNDERPANTS AND METHOD FOR PRODUCING THE SAME

BACKGROUND OF THE INVENTION

1. Technical Field of the Invention

The present invention relates to protective pants and to a method of producing the same. Prior Art Protective pants of this generic type are known from WO 98/43503. These protective pants are underpants and have a so-called barrier for a fluid in that region of the same which is assigned to the genital area of the person using the pants. This barrier is made up of material layers which are located one upon the other and of which one can absorb the fluid. The barrier is virtually impermeable for a fluid, it occupies a region of the front side of the underpants, and it is sewn into said region of the pants, with the result that said barrier constitutes a section of the front wall of the pants. The individual layers of said barrier are comparatively thin. If the quantity of fluid passing out of the body of the person wearing said pants exceeds a certain amount, then the thin barrier is no longer able to absorb this quantity of fluid and the quantity of body fluid which has not been absorbed escapes from the pants, all the more so since the fluid can also seep through the underpants seams with the aid of which the barrier is connected to the rest of the protective pants.

2. Object of the Invention

The object of the present invention is to fabricate protective pants so that virtually no fluid can escape from them.

BRIEF DESCRIPTION OF THE DRAWINGS

Embodiments of the present invention are explained in more detail hereinbelow with reference to the attached drawings, in which.

DETAILED DESCRIPTION OF THE PREFERRED EMBODIMENT(S) OF THE INVENTION

Figure 1:
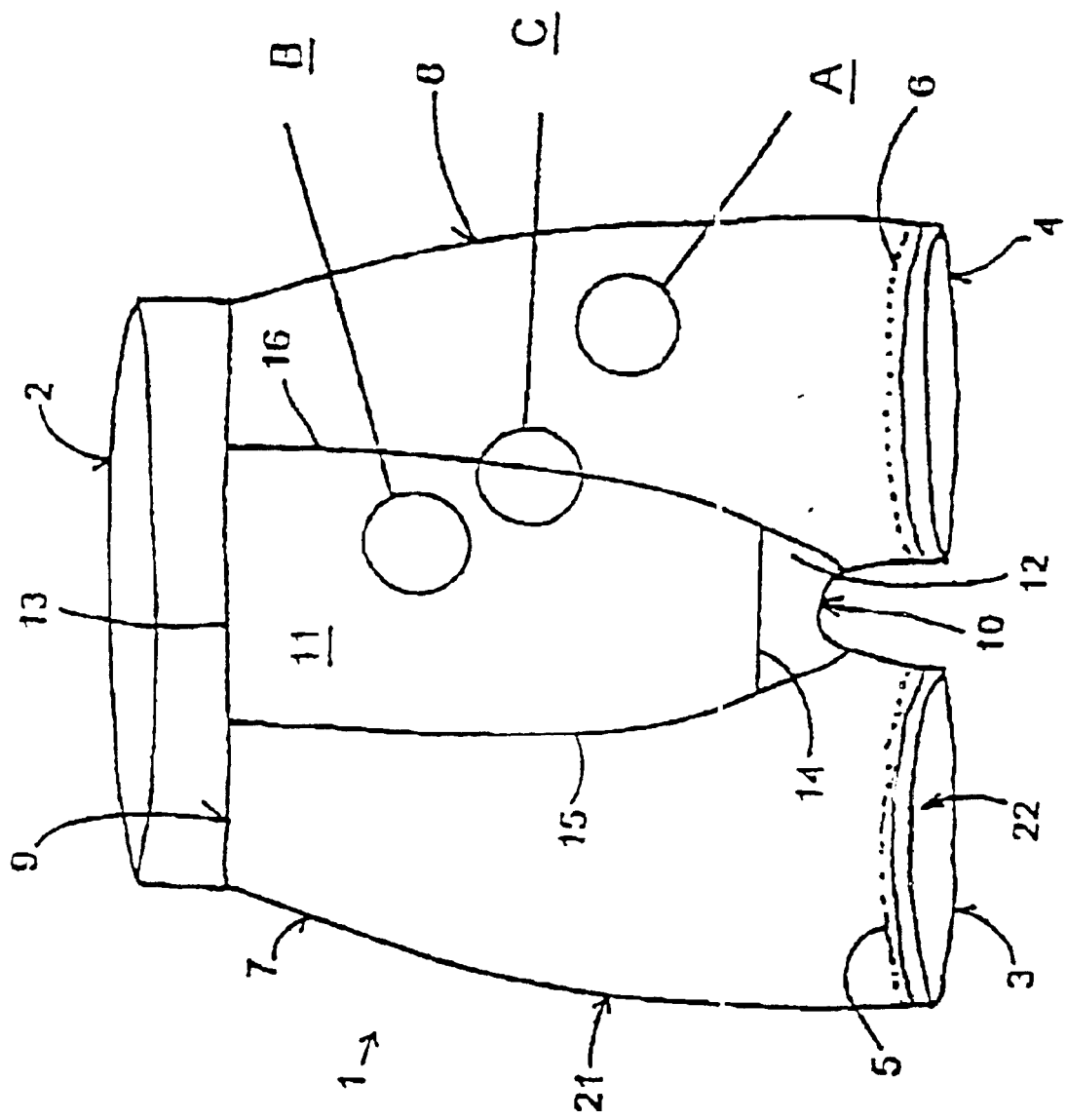
FIG. 1 shows a front view of a first embodiment of the present protective pants, of which the basic body is made up of an outer part and of an inner part.
Figure 8:
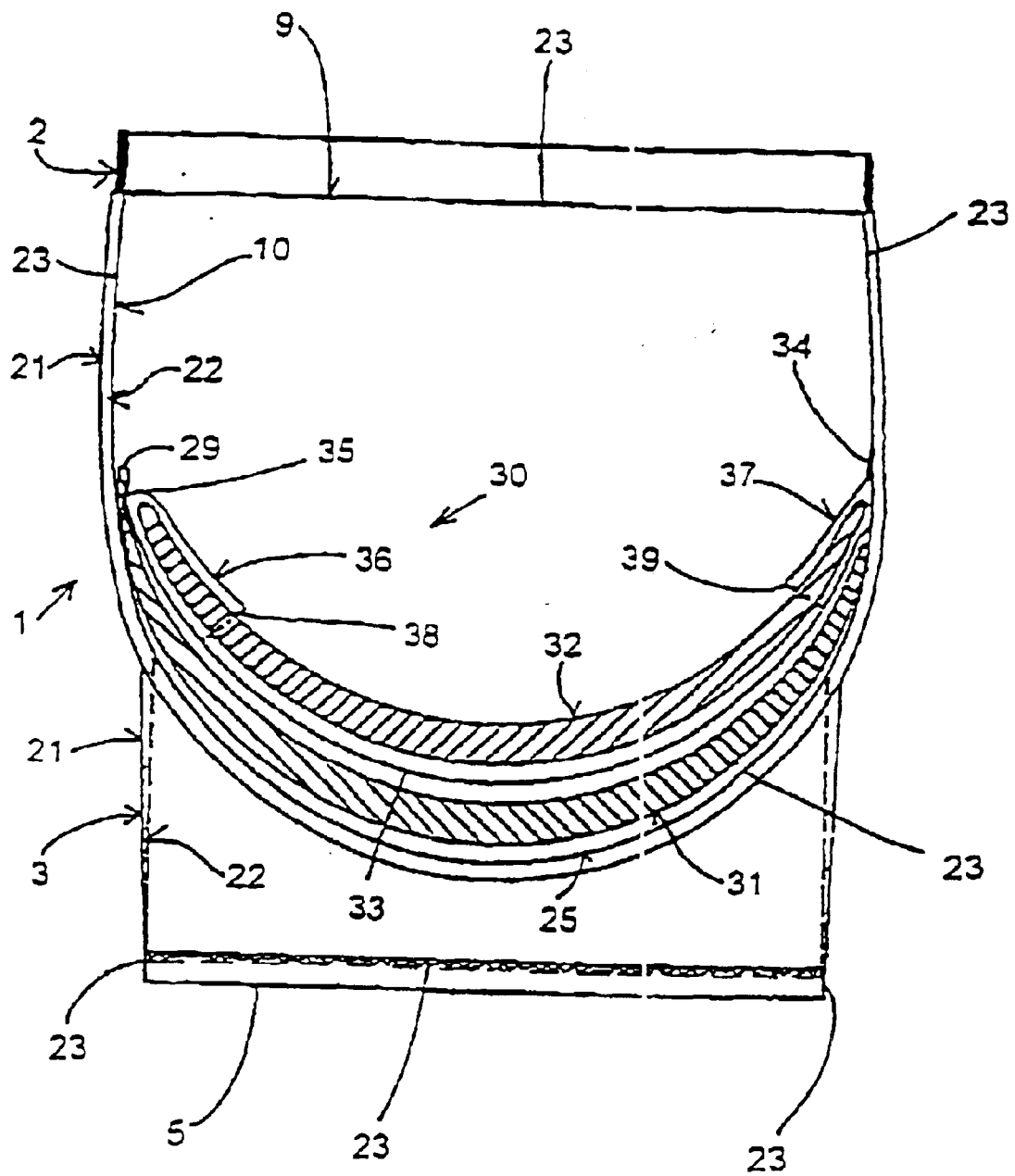
FIG. 8 shows the protective pants according to FIG. 1 in a vertical longitudinal section.

The protective pants illustrated in FIGS. 1 and 8 have a basic body 1, of which the shape corresponds to the shape of the basic body of ordinary underpants. An elastic waistband 2 which is known per se is connected, for example by sewing, to the top opening 9 of the basic pants body 1. In the case illustrated, said waistband 2 is designed as a flat strip which is connected to the basic pants body 1 via one of its longitudinal edges. In the case of the pants illustrated in FIG. 1, the basic pants body 1 has legs 3 and 4. Leg seams 5 and 6 which are known per se are provided in the free border region of said legs 3 and 4.

The basic pants body 1 comprises an outer part 21 and an inner part 22, which are of essentially identical design. The inner part 22 is arranged in the interior of the outer part 21. FIG. 1 illustrates the present protective pants in the completed state and, as a result, the inner part 22 of the basic pants body 1 cannot be seen from FIG. 1. This inner part 22 is illustrated together with the outer part 21 in FIG. 8 and on its own in FIGS. 5 to 7.

The present protective pants are produced such that the outer part 21 and the inner part 22 of the basic body 1 of the protective pants are produced separately. The inner part 22 is then positioned in the outer part 21 and said parts 21 and 22 are connected together in the regions of the waistband 2 and of the pants-leg openings 3 and 4. In this way, the waistband 2 may be connected to the basic body 1 at the same time.

The respective part 21 or 22 of the basic body 1 of the pants comprises two side parts 7 and 8 and a central part 10 arranged therebetween. The side parts 7 and 8 of the basic body 1 are intended for resting on the sides of the human torso, in the region of the pelvis thereof. The outline of these side parts 7 and 8 is also shaped accordingly. The outer contour of blanks (not illustrated) from which the side parts 7 and 8 are produced has a first and more or less rectilinear section, which is located in the waist region 2 of the pants. This section of the outline of the blank is located on the line bounding the top opening 9 of the basic pants body 1.

Extending down from the ends of the first contour section or of the waist section of the side parts 7 and 8 are in each case two further sections 15 and 16 of the contour of the respective side part 7 and 8, by which the side parts 7 and 8 are connected to the r central part 10. The longitudinal edges of the central part 10, via which the latter is connected to the side parts 7 and 8, have a profile corresponding to the profile of said contour sections 15 and 16 of the side parts 7 and 8. If the pants have legs 3 and 4, as is the case with the pants according to FIGS. 1 to 8, then the second or further sections 15 and 16 of the contour of the side parts 7 and 8 run such that they enclose that material of which, inter alia, the pants legs also consist. The contours of the side parts 7 and 8 are of mirror-inverted configuration, it being possible for these contours otherwise to be at least essentially identical.

The central part 10 runs through the crotch region of the pants and is made up of two elongate sections 11 and 12 arranged one behind the other. Said sections 11 and 12 are of different lengths. The central-part section 11, which is located on the front side of the pants, is shorter than the central-part section 12, which is located predominantly in the rear region of the pants. The transverse edges 13, which are located at the free ends of the central-part sections 11 and 12, are likewise located on that line which bounds the top opening 9 of the basic pants body 1. One of these end edges 13 is located in the front region of the pants and the other end edge 13 is located in the rear region of the pants. The respective end edge 13 of the central part 10 is located between the waist sections of the contour of the blank of the side parts 7 and 8, with the result that the end edges 13 of the central part 10 close the gaps between the-waist sections of the contour of the side parts 7 and 8 and also bound the top opening 9 in the basic pants body 1. The top border 9, put together in this way, of the basic pants body 1 is connected to the bottom border of the waistband 2.

The inner edge 14 of the front central-part section 11 is located in the front region of the pants because the front section 11 of the central part 10, as has been explained above, is shorter than the rear section 12 of the central part 10. The inner edge is connected to the inner transverse edge of the rear and longer central-part section 12, so that said inner edge cannot be illustrated separately in FIG. 1. Connecting locations between the central part 10 and one of the side parts 7 and 8 of the pants extend along the longitudinal borders 15 and 16, respectively, of the central part 10. Said connecting locations 15 and 16 may be configured, for example, as seams. The borders 13, 15 and 16 of the central part 10 are connected both to the waistband 2 and to those borders of the side parts 7 and 8 which are facing or are assigned to said central part 10.

For said connections or for connecting the individual sections 2, 7, 8, 10, 11 and 12 of the basic body of the pants to one another, techniques other than sewing, for example adhesive bonding, sealing, etc., are also possible.

Figure 5:
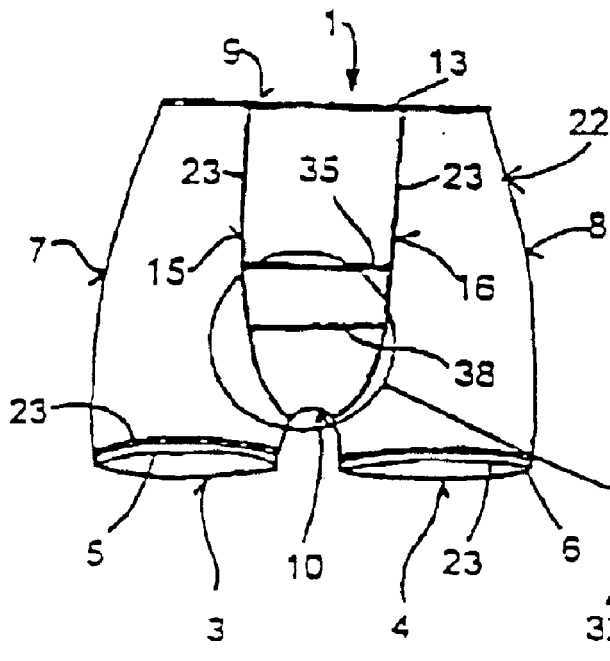
FIG. 5 shows a front view of the inner part of the basic body of the protective pants according to FIG. 1.
Figure 7:
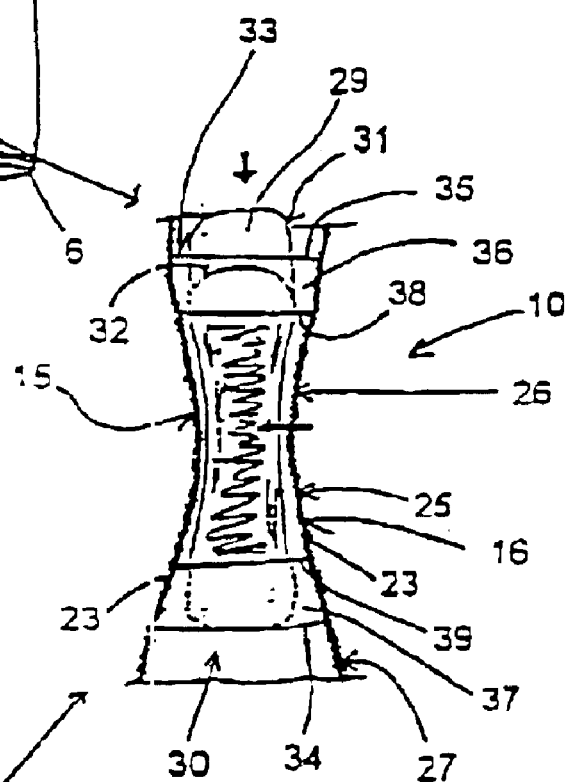
FIG. 7 shows a plan view of a detail from the inner side in the crotch region of the inner part of the pants according to FIGS. 5 and 6.
Figure 6:
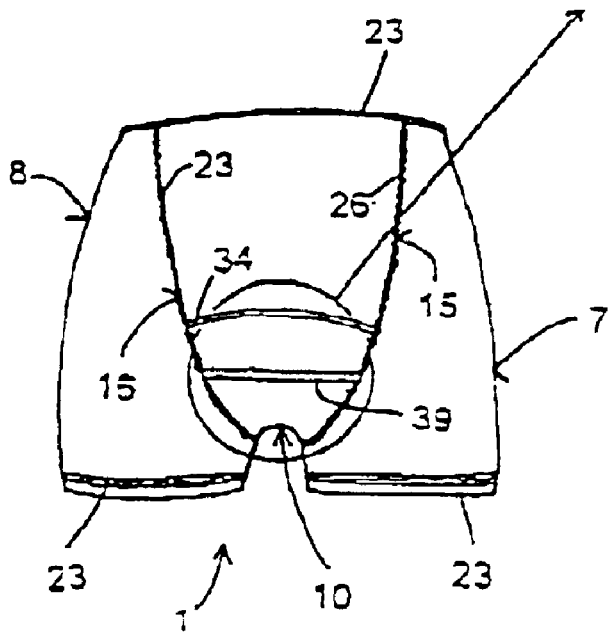
FIG. 6 shows a rear view of the inner part from FIG. 5.

FIG. 5 shows a front view of the inner part 22 of the basic body 1 of the present protective pants. FIG. 6 shows a rear view of said inner part 22. FIG. 7 shows a plan view of a detail from the inner side of the crotch region of the inner part 22 according to FIGS. 5 and 6. FIG. 8 shows the protective pants according to FIG. 1 in a vertical longitudinal section.

As has been mentioned, the outer part 21 and the inner part 22 of the basic body 1 of the present pants may be of identical design, FIG. 8 showing how the inner parts 22 are arranged in the outer pants 21. The inner part 22 likewise has the side parts 7 and 8 and the central part 10. In the case illustrated, the central part 10 of the inner pants 22 is integral, with the result that said central part 10 does not have a transverse seam 14. The inner pants 22 also have the longitudinal connections 15 and 16 extending along the mutually associated locations at the edges of the side parts 7 and 8 ad at the edges of the central part 10.

The parts 21 and 22 of the present protective pants are only connected to one another in the region of the waistband 2 and of the bottom openings 5 and 6 of the pants. Therebetween, the materials of the pants parts 21 and 22 rest loosely upon or against the other, as can be seen, for example, from FIGS. 2 to 4.

Sealing strips 23 (FIGS. 5 to 8) are provided and cover over, inter alia, the seams at which two constituent parts of the inner pants 22 meet. In the case of the inner pants 22, the sealing strips 23 also cover over, inter alia, the seams 15 and 16 between the central part 10 and the side parts 7 and 8 and also the seam 14 within the central part 10. The sealing strips 23 are provided on the outer side of the inner part 22 of the present protective pants. Such sealing strips 23 are also located in the region of the waistband 2 and in the region of the pants legs 3 and 4, to be precise between the outer pants 21 and the inner pants 22, where they seal those locations of the protective pants at which the borders of the outer pants 21 and of the inner pants 22 rest one upon the other.

The sealing strips 23 may be configured as adhesive strips or as strips of a material which becomes soft or semi-liquid under the action of heat. The softened material penetrates into the depressions located beneath it, fills these and, following cooling, the material of such strips 23 ensures that the seams between two adjacent constituent parts of one of the parts 21 or 22 of the protective pants and the gaps between the pants parts 21 and 22 are fluid-tight.

The peripheral contour of the central part 10 (FIG. 7) of the outer pants 21 and of the inner pants 22 is essentially in the form of the outline of an hourglass, only the central section of the central part 10 being illustrated in FIG. 7. This outer contour of the central part 10 has a narrowest location 25, which is located directly in the crotch region of the protective pants. The respective end portion of said narrowest location 25 is adjoined by widened sections 26 and 27 of said contour of the central part 10. In each case one of the abovementioned transverse or end edges of the central part 10 is located at the end of the respective wide section 26 or 27 of the central part 10, said transverse or end edge being located on the line bounding the top opening 9 of the basic pants body 1. The longitudinal edges 15 and 16, of which the profile has already been described, extend between said end edges of the central part 10.

The inner side, i.e. the side directed toward the body, of the central part 10 of the inner pants 22 has means 30 for securing elongate liners 31 and 32 located one above the other, it being possible for said liners to be of a type known per se. The first part of the retaining means 30 is configured as an elongate compartment (FIGS. 7 and 8), the longitudinal direction of said compartment coinciding with the longitudinal direction of the central part 10. Said compartment is formed by an upper wall 33, from a textile material which rests on the top side or inner side of the central portion 25 of the central part 10. The end portions of said upper wall 33 are located in the region of the wide portions 26 and 27 (FIG. 7) of the central part 10 and cover over those sections of the wide portions 26 and 27 of the central part 10 which adjoin the narrowest location 25.

The profile of the longitudinal borders of said upper wall 33 corresponds to the profile of the edges 15 and 16 of the central part 10, said borders of the upper wall 33 being connected, for example by sewing, to the material of the central part 10 of the inner pants 22. The end edge 34 of the upper wall 33, said end edge being located in the rear region of the protective pants and running transversely to the longitudinal direction of the central part 10, is connected to the material of the central part 10, to be precise, for example, likewise by sewing. The front edge 35 of the upper wall 33, said front edge being located in the front region of the pants, is not connected to the central part 10, this providing an opening through which the first liner 31 can be introduced into said compartment 33. The rear end of said first liner 31 is then located in the region of the rear edge 34 of said compartment 33. In the case illustrated, the length of the upper wall 33, and thus also of said compartment, is smaller than the length of the liner 31, with the result that a section 29 of the first liner 31 projects from the compartment 33 at the front. However, it is also possible for the length of the upper wall 33 to be the same as the length of the liner 31.

Provided for the purpose of securing the second liner 32, which is located above the first liner 31, are pockets 36 and 37 which are intended and designed for accommodating the end portions of the second liner 32. The respective pocket 36 or 37 is formed by an essentially quadrilateral section of a textile material which is fastened on that side of the upper wall 33 of the compartment which is directed toward the body.

The first material section 36 is provided on the front section of the upper wall 33, where the insertion opening 35 for the first liner 31 is located. In this case, the front edge of said first material section 36 is virtually flush with the free front edge 35 of the upper wall 33. The front edge and the side edges of said first material section 36 are connected, for example by sewing, to the material of the upper wall 33. Since that edge 38 of said material section 36 which is closer to the other end of the upper wall 33 is not connected to the upper wall 33, said pocket 36 has an opening here through which one of the end portions of the second liner 32 can be introduced into said pocket 36.

The second material section 37 is provided on the rear section of the upper wall 33, where the rear transverse edge 34 of the compartment 33 is located, said transverse edge adjoining the material of the inner pants 22. The rear edge of said material section 37 is connected to the material of the inner pants 22 together with the rear edge 34, located here, of the upper wall 33. Since the front edge 39 of said material section 37 is not connected either to the upper wall 33 or to the material of the inner pants 22, an opening for this pocket 37 is provided in the region of said front edge 39, and the second end portion of the second liner 32 can be introduced into said pocket 37 through said opening. The second liner 32 is shorter than the distance between the edges 34 and 35 of the upper wall 33, with the result that said liner 32 fits easily into the retaining device configured in this way. In the case illustrated, the second liner 32 is shorter than the first liner 31. It is also possible, however, for these liners 31 and 32 to be of the same length and also otherwise identical.

Figure 2:
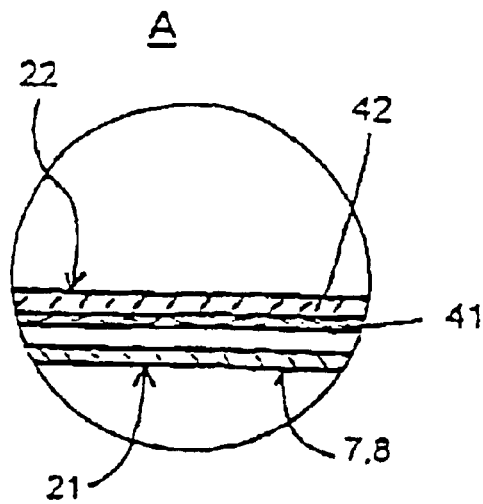
FIGS. 2 to 4 show, in a horizontally running section, details from three regions of the protective pants according to FIG. 1.
Figure 3:
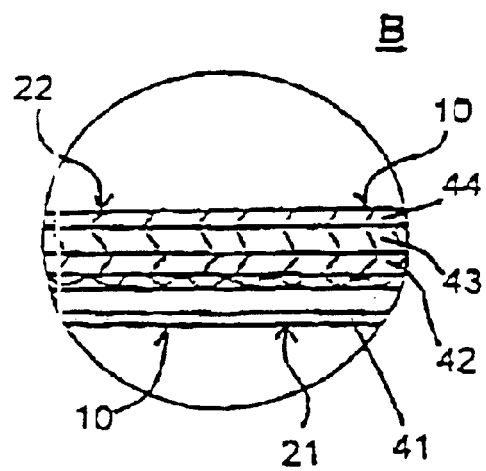
Figure 4:
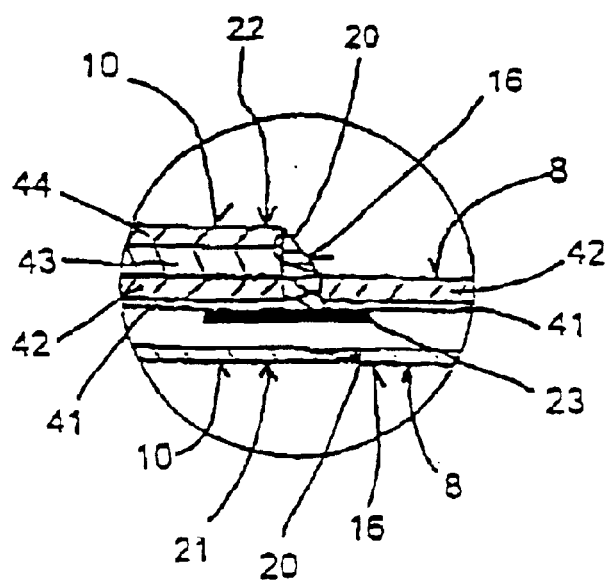

FIGS. 2 to 4 show, in a horizontally running section, details from three regions of the protective pants according to FIG. 1 FIG. 2 shows a detail from one of the side regions 7, 8 of the protective pants. One of the pants legs 3, 4, respectively, may be located in the bottom section of the respective side region of the protective pants.

The detail according to FIG. 2 comprises a detail from the outer pants 21 and a detail from the inner pants 22, these running virtually parallel to one another. In order to make it more clear that two constituent parts 21 and 22 of the pants, said constituent parts being positioned one inside the other, are concerned here, the details of these constituent parts 21 and 22 of the pants are illustrated at a distance apart from one another. The side parts 7 and 8 of the outer pants 21 are formed by a top material which is normally used in the production of underpants. Consequently, the present protective pants, at first glance, initially resemble ordinary underpants. This material may advantageously be a cotton material.

The material of the side parts 7 and 8 of the inner pants 22, in contrast, comprises a protective material which, in the present case, has two layers of different materials. A layer 41 of a fluid-impermeable material is located on the outer side of the inner pants 22. This layer 41 may be configured, for example, as a membrane of polyurethane, because such a membrane, although fluid-impermeable, is breathable. Said outer layer 41 is located on that side of the inner pants 22 which is directed toward the outer pants 21. Located on the inner side of the side part 7 or 8 of the inner pants 22 is an inner material 42 which is absorbent and skin-compatible. This material 42 may be made of filaments which contain a mixture of cotton and polyester fibers or cotton and polyamide fibers. These may be mixtures known per se of said fibers.

FIG. 3 shows a detail from the central region of the protective pants where the central part 10 is located both in the case of the outer pants 21 and in the case of the inner pants 22. The central part 10 of the outer pants 21 is made of the same material as the side parts 7 and 8 of the outer pants 21, as has been described in conjunction with FIG. 2. Since the majority of the fluid passing out of the body of the person using the protective pants is to be stored in the central part 10 of the inner pants 22, the protective material of said central part 10 has a multi-layered structure. The already mentioned fluid-tight material 41 is located on the outer side of the inner pants 22. The inner material 42, which has likewise already been mentioned above and may contain cotton and polyester, is arranged on the inner side of said outer layer 41.

Located on the inner side of the inner material 42 is a material 43 which has the highest possible absorbency and/or capacity to store the fluid passing out of the body. This material layer 43 may be made, for example, of a double terry material. Moreover, this material layer may either be provided with odor-inhibiting means and/or it may be woven or knitted with odor-inhibiting yarns.

That surface of the absorbent-material layer 43 which is directed toward the body is provided with a further material layer 44. This material layer 44 is made of a material which may also be referred to as a transporting material. This material 44 may likewise be produced from odor-inhibiting yarns, for example of polyester or of microfibers. This material allows fluids to flow through the interior of this protective material 44 only from its free surface, as a result of which the skin of the person using the protective pants is prevented from getting wet by the fluid flowing back out of the layer 43. The user's skin thus remains essentially dry. The surface of said transporting material 44 which is directed toward the user's body is skin-compatible. The material 44 itself is of such a nature that it cannot adhere to the body of the person wearing the protective pants once the fluid has passed out of a body orifice and then dried.

FIG. 4 illustrates a detail from one of the transition portions between one of the side parts 7, 8 and the central part 10 of the outer pants 21 and the inner pants 22. The side part 8 illustrated and the central part 10 of the outer pants 21 are produced from said conventional material for underpants, as has been described above. The side part 8 of the inner pants 22 which is illustrated has only the two layers 41 and 42 already described above. The central part 10 of the inner pants 21 has all four layers 41 to 44 described above. The connection of the parts 8 and 10 of the outer pants 21 in the region of the connecting location 16 on the outer pants 21 takes place with the aid of a seam 20. The central part 10 and the side part 8 of the inner pants 22 are connected to one another in the region of the connecting location 16 likewise with the aid of a seam 20. The above-described sealing strip 23 is provided on the outer side of the seam 20 and the connecting location 16 of the inner pants 22, said sealing strip being wider than the seam 20.

It goes without saying that these explanations also apply analogously to the rest of the protective pants. The sealing strips 23 are also located in the region of the waistband 2 and of the pants legs 3 and 4, as has already been explained. These strips 23 may be made, for example of polyurethane, which becomes soft to viscous under the action of heat.

The present protective pants may be used as an item of underwear, and for sports and medical purposes, etc. They are fluid-impermeable, absorbent, sealed and nevertheless breathable. Moreover, the protective pants are configured such that they maintain their useful properties even after being washed a number of times. Said pants may be worn by people who are mildly, moderately or severely incontinent but not bedridden, the use of the above-described liners 31 and 32 being appropriate, in particular, for the severely incontinent.

Figure 9:
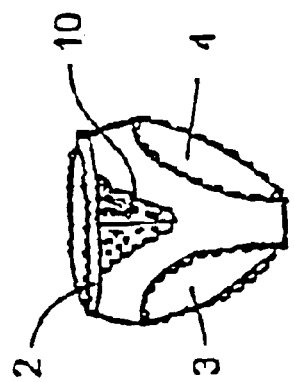
FIGS. 9 to 16 show a front view of further embodiments of the protective pants.
Figure 10:
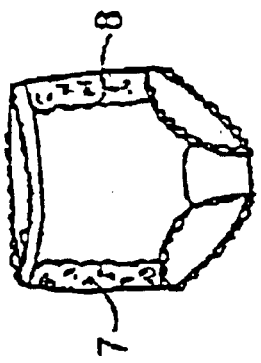
Figure 11:
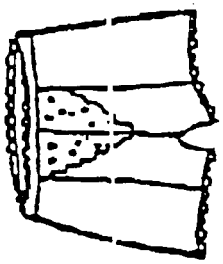
Figure 12:
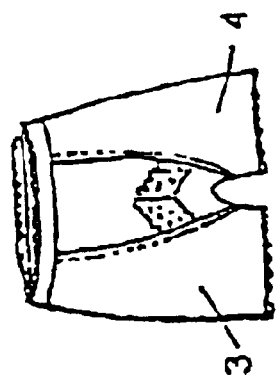
Figure 13:
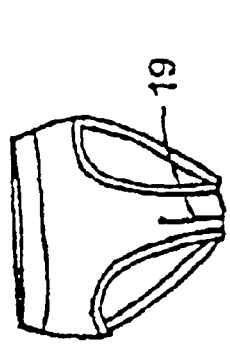
Figure 14:
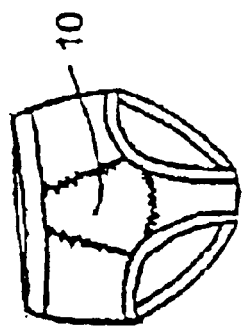
Figure 15:
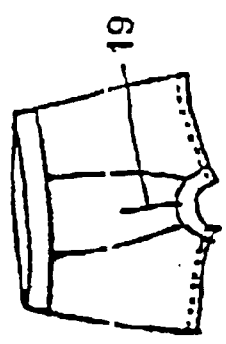
Figure 16:
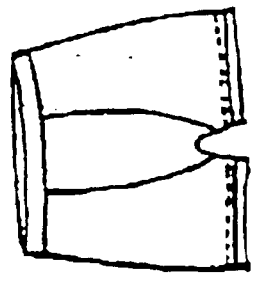

Such protective pants may have different cuts. It is possible to distinguish, by way of these cuts, between the protective pants for women, men and children, in which case it is likewise possible to distinguish between the protective pants for girls and for boys. FIGS. 9 to 16 illustrate some of the protective pants having different cuts. In these figures: FIG. 9 shows ladies' panties, FIG. 10 shows panty briefs for ladies, FIG. 11 shows long-leg ladies' panties, FIG. 12 shows ladies' shorts, FIG. 13 shows men's briefs, FIG. 14 shows classic briefs for men, FIG. 15 shows shorts and FIG. 16 shows boxer shorts. The ladies' panties according to FIG. 9 have decorative detail, embroidery in the case illustrated, in the region of the high-cut leg openings 3 and 4 and in the region of he waistband 2 and of the central part 10. The panty briefs according to FIG. 10 also have decorative detail 1 the region of the side parts 7 and 8. A decorative-detail section is inserted in the central part 10 of the classic briefs for men according to FIG. 14.

Figure 17:
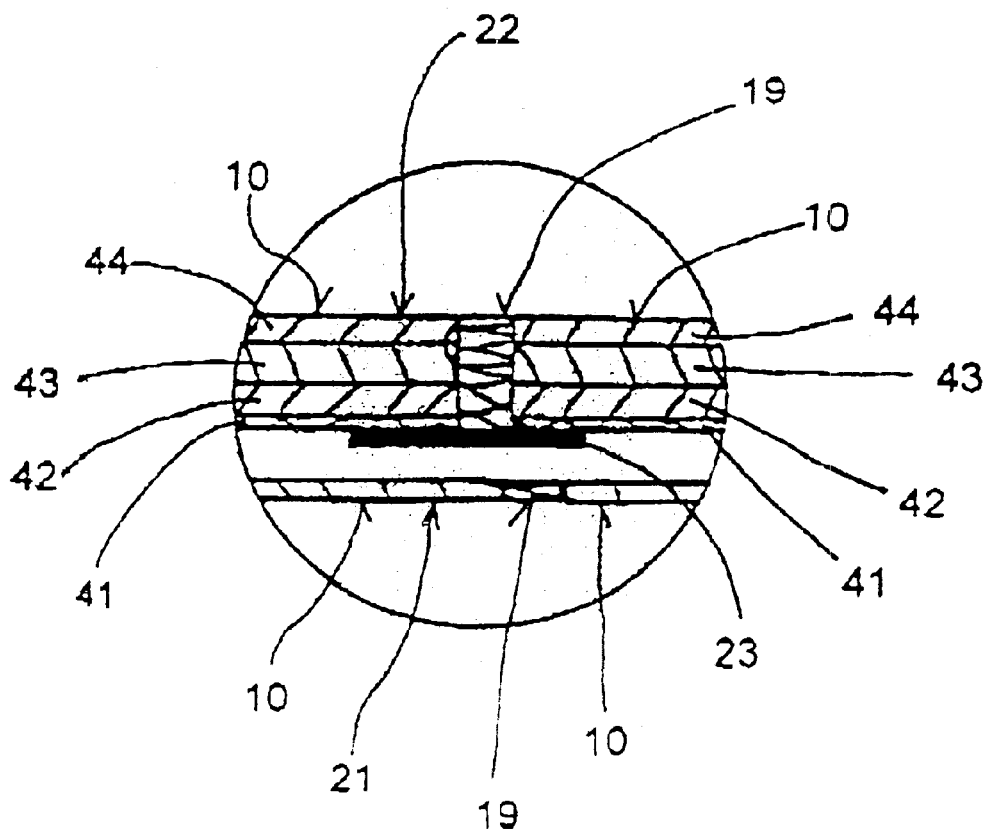
FIG. 17 shows, in a horizontally running section, a detail from the crotch regions of a central portion of the protective pants according to FIG. 13.

In order to achieve a better fit of the protective pants, at least one of the pants parts 21 and/or 22 may be provided with a longitudinal seam 19 (FIGS. 13 and 15) in the crotch region. FIG. 17 shows, in a horizontal section, a detail from the crotch regions of the central portion 10 of the protective pants. The adjacent sections of the central part 10 of the inner pants 22 which are connected to one another by the longitudinal seam 19 have all four of the abovementioned layers 41 to 44 because the opening in the central part 10 which is closed by the longitudinal seam 19 has been produced merely by removal of a section of the central part 10. The same applies to the outer pants 21. The above-described sealing strip 23 is provided on the outer side of the longitudinal seam 19 in the inner pants 22.

Figure 18:
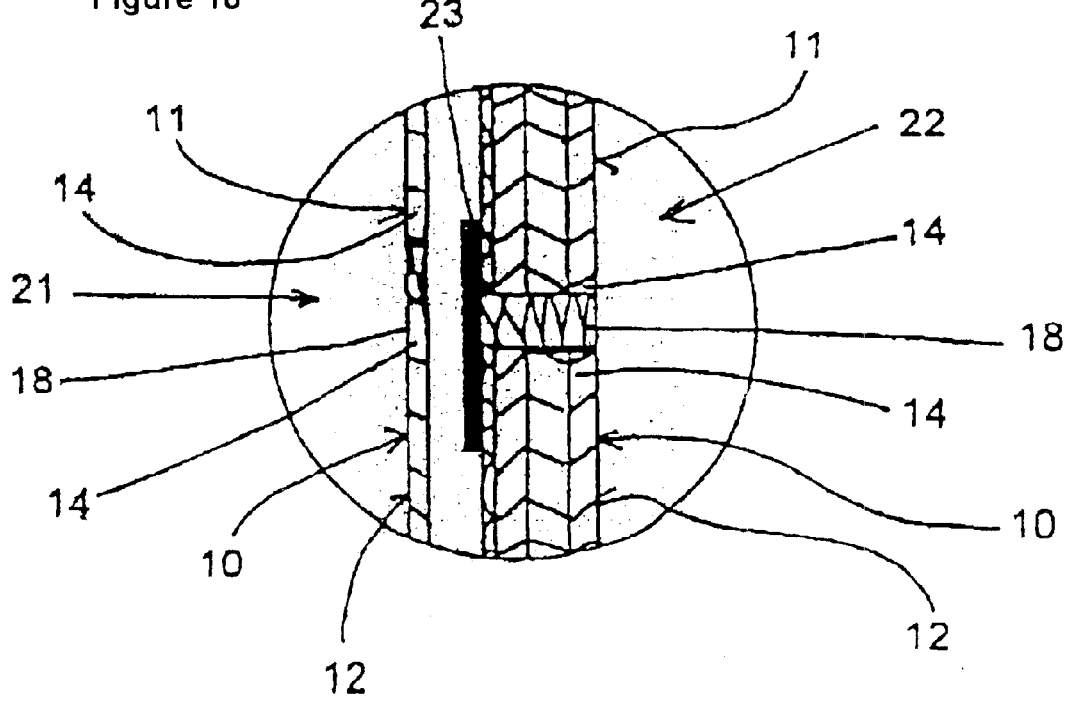
FIG. 18 shows, in a vertically running section, a connecting location within a two-part central portion of the protective pants.

FIG. 18 shows, in a vertically running section, the connecting location 14 within the central portions 10, comprising two sections 11 and 12, of the outer pants 21 and of the inner pants 22 with the transverse seam 14 in the inner pants 22. The transverse seam 20 present here is sealed on the outer side of the inner pants 22 with the aid of a further sealing strip 23.

What is claimed is:

1. Protective pants configured so that virtually no fluid can escape from them comprising
   a basic body (1), having an outer part (21) and an inner part (22) which are of substantially identical design, the inner part arranged in an interior of the outer part (21), the outer part and the inner part connected to one another at a waist region (9) and at leg openings (3, 4) of the protective pants and respectively having two mutually opposite side parts (7, 8) and a central part (10) arranged therebetween, the side parts (7, 8) each having a first border portion which is located in the waist region (9) extending away from ends of the first border portion, and a second border portion (15, 16),
   wherein the central part (10) has longitudinal edges which are connected to the second border portions (15, 16) of the side parts (7, 8),
   wherein the central part (10) runs through a crotch region of the protective pants, and has transverse edges (13) on free ends thereof, located in the waist region, one of the edges being at a front of the waist region and the other of the edges (13) being located at the rear of the waist region, the transverse edges (13) being located between the first border portions, a border of the waist region (9) comprising the transverse edges and the first border portions being connected to a waistband (2),
   wherein the central part (10) is made up of a first and a second elongate section (11, 12) arranged one behind the other, the first elongated section (11) which is located on a front side of the protective pants is shorter than the second elongated section (12) which is located substantially in a rear side of the protective pants, the first and second elongated sections (11, 12), being connected together at an inner connecting location (14),
   wherein said inner connecting location (14) is located at the front side of the protective pants.

2. The protective pants as claimed in claim 1, wherein sealing strips (23) are provided which cover over seams (14, 15, 16) on an outer side of the inner pants (22) produced by connecting the central part to the side parts and the first elongated section to the second elongated section.

3. The protective pants as claimed in claim 1, wherein a peripheral contour of the central part (10) of the outer pants (21) and of the inner pants (22) is substantially in a form of an outline of an hourglass, a narrowest location (25) of the central part (10) is located directly in the crotch region of the protective pants, respective end portions of said narrowest location (25) are adjoined by widened sections (26, 27) of the central part (10), the transverse edges (13) of the central part (10) being respectively located on free ends of the widened sections (26, 27), and wherein the second border portions (15, 16) extend between the transverse edges (13) of the central part (10).

4. The protective pants as claimed in patent claim 1, wherein a side of the central part (10) of the inner pants (22) is directed toward a user and has retaining means (30) for securing elongate liners (31, 32) located one above the other, a first part of the retaining means (30) is designed for accommodating the first liner (31), is configured as an elongate compartment, the longitudinal direction of said compartment coinciding with the longitudinal direction of the central part (10), said compartment being formed by an upper wall (33) which engaged on an inner side of a central portion of the central part (10), the end portions of said upper wall (33) being located in the region of the widened sections (26, 27) of the central part (10).

5. The protective pants as claimed in claim 4, wherein a profile of longitudinal borders of the upper wall (33) corresponds to a profile of the second border portions (15, 16) of the central part (10), said longitudinal borders of the upper wall (33) are connected to material of the central part (10) of the inner pants (22), an end edge (34) of the upper wall (33) located in the rear side of the protective pants and running transversely to the longitudinal direction of the central part (10), is connected to the material of the central part (10), a front edge (35) of the upper wall (33) located at the front side of the protective pants, is not connected to the central part (10).

6. The protective pants as claimed in claim 4, wherein pockets (36, 37) are provided for the purpose of securing the second liner (32), the pockets being intended and designed for accommodating end portions of the second liner (32), said pockets being provided on the upper wall (33) of the compartment, one of the pockets (36, 37) being located at one end of the upper wall (33) of the compartment, where the respective pocket is fastened.

7. The protective pants as claimed in claim 1, wherein strips (23) are provided in the region of the pants legs (3, 4) between the outer pants (21) and the inner pants (22), where they seal locations of the protective pants at which borders of the outer pants (21) and of the inner pants (22) rest against each other.

* * * * *